United States Patent [19]

Fitzky

[11] 4,155,035

[45] May 15, 1979

[54] DEVICE FOR THE MEASUREMENT OF THE MOISTURE CONTENT OF A SAMPLE

[75] Inventor: Hans-Georg Fitzky, Odenthal-Hahnenberg, Fed. Rep. of Germany

[73] Assignee: Bayer Aktiengesellschaft, Leverkusen, Fed. Rep. of Germany

[21] Appl. No.: 741,575

[22] Filed: Nov. 12, 1976

[30] Foreign Application Priority Data

Nov. 26, 1975 [DE] Fed. Rep. of Germany ....... 2552954

[51] Int. Cl.² .......................................... G01R 27/04
[52] U.S. Cl. .............................................. 324/58.5 C
[58] Field of Search .................... 324/58.5 C, 58.5 B, 324/58 B, 58 C

[56] References Cited

FOREIGN PATENT DOCUMENTS 2221213  11/1973  Fed. Rep. of Germany ........ 324/58 C
1115129   5/1968  United Kingdom .................. 324/58 B
1180843   2/1970  United Kingdom ............... 324/58.5 C
 381039   8/1973  U.S.S.R. .............................. 324/58.5 C

*Primary Examiner*—Stanley T. Krawczewicz
*Attorney, Agent, or Firm*—Sprung, Felfe, Horn, Lynch & Kramer

[57] ABSTRACT

The damping of a microwave resonator by the sample to by examined is used as a measurement for the moisture content of the sample. In this arrangement use is made of a microwave generator whose frequency range is selected so that the complete resonance curve of the resonator both when empty and when supplied with the sample is covered. The measurement head containing the resonator is in the form of an insertion and immersion probe and consists of a one part cavity resonator which is provided at the point of maximum electrical or magnetic field strength with a perforation having a diameter of $\phi < 0.5\lambda$ ($\lambda$=microwave length). Through this perforation a scattered electrical field passes into the sample applied to it or guided over it.

14 Claims, 10 Drawing Figures

DEVICE FOR THE MEASUREMENT OF THE MOISTURE CONTENT OF A SAMPLE

This invention relates to a device for the measurement of the moisture content of a sample, e.g. paper, wood, brick work, soil etc. The measurement is based on the microwave absorption of water. The device consists of a frequency modulated microwave generator, whose frequency variation is adjusted so that the whole resonance curve of the cavity resonator both when empty and when containing the sample is covered. The frequency modulated microwave generator supplies a resonator whose damping by the sample is a measurement of the moisture content of the sample under examination. A microwave detector is arranged after the resonator to pick up the reflected or transmitted microwave signal.

Moisture measurement devices based on the principle of microwave absorption are known. German Offenlegungsschrift 2,340,130 describes a method in which samples in strip form (e.g. paper or film webs) are continuously monitored in respect of their water content on the basis of microwave absorption. In this method the sample in strip form is continuously passed through the separation gap of a two part resonator. The resonator is supplied by a frequency modulated microwave generator and the frequency variation is selected so that the whole resonance curve of the resonator both when empty and when filled with the sample is covered. The resonator is detuned by the sample so that the resonance frequency is pushed down to lower values. As a measurement value for the water content the quality factor change of the resonator is used. Either the signal reflected by the resonator or the transmission signal can be picked up.

This method has proved very effective in the measurement of strip form samples. However a major disadvantage of this arrangement is that only those samples which can be passed through the resonator or which are so small that they can be introduced into the resonator can be measured. The method is, however, restricted to flat or very small samples. However from a technical point of view the measurement of moisture in spatially extended samples is of quite considerable interest. The term "spatially extended" should here be understood as meaning that the sample material has only one surface for the application of the measurement head but otherwise has any desired spatial extent. Typical examples thereof are wooden parts, chipboard panels, concrete walls, brick work, bales of material, paste paints etc. In addition there is, for example, in the food stuffs industry the necessity for moisture measurements on powder, paste or granulate form goods. Examples which might be mentioned here includes the determination of the residual moisture content of powdered milk, powdered coffee or tobacco. In these cases the measurement head must be designed in such a way that it is surrounded by the product to be investigated.

Hitherto no microwave measurement methods have been known for such samples.

The object of the invention therefore is to develop a moisture measurement device suitable for such samples, starting from the initially mentioned microwave measurement method.

According to the invention, there is provided a device for the measurement of the moisture content of a sample comprising a frequency modulated microwave generator which supplies a resonator whose damping by the sample is a measurement of the moisture content of the sample and the frequency range of the microwave generator is selected so that the complete resonance curve of the resonator both empty and when supplied with the sample is covered and a microwave detector for the microwave signal reflected or transmitted by the resonator is arranged after the resonator, wherein a measurement head containing the resonator is in the form of an application or immersion probe and the resonator consists of a one-part cavity resonator, which at the point of maximum electrical or magnetic field strength is provided with a perforation having a diameter $\phi < 0.5 \ \lambda$ where $\lambda$ = microwave length, through which a scattered electrical field passes out into the sample applied to it or guided over it.

Initially it was not to be expected that a usable microwave moisture measurement device could be devised in this way. Because of the perforation in the resonator wall firstly microwave energy is able to pass outwards and reduce the measurement sensitivity by the reduction of the quality factor as a result of radiation damping. Secondly by the reflection of the radiation let out, particularly on moving objects in the surrounding area, sound waves are generated which reduce the measurement accuracy by a feed back effect on the measurement resonator.

However, contrary to expectation the microwave moisture measurement devices according to the invention are relatively insensitive to this interference and achieve a remarkably high measurement accuracy of the order of magnitude of 3% of the measurement range final value.

The resonator is preferably a rectangular resonator in which the $TE_{10}$ field type is excited. The issuing scattered electrical field has a practically completely symmetrical radial distribution in the resonator, if dumped out at (the place of) an E-field maximum, which avoids an anisotropic effect of the microwave absorption in materials with oriented structures, e.g. fibre bundles, paper, chipboard panels.

Alternatively, a cylindrical resonator with the $TE_{11}$ field type can also be used, the perforation being arranged at the point of an TE field maximum.

A significant improvement of the invention consists in a conductor in the form of a wire being arranged in the centre of the perforation in the resonator parallel to its longitudinal direction, whose length corresponds approximately to the diameter of the perforation. In this way the scattered field passing through the perforation can be concentrated better into the sample. This may become necessary if the sample comprises for example a panel and without additional assistance the scattered field would pass through the panel into free space. The damping of the resonator would then be conditioned not only by the dielectric losses in the sample but also by radiation out into free space.

Instead of one wire, a plurality of wires or a plurality of neighboring bores of smaller diameter in the resonator wall can be used. This effects the attenuation of the scattered field within a very short distance from the resonator.

In order to prevent parts of a sample from falling into the resonator, the perforation can usefully be covered with a Teflon disc (polytetrafluorethylene). For the same reason one might also consider filling the resonator entirely with polytetrafluoroethylene as a dielectric. At 10 Gigahertz this material is practically loss-free.

The two last mentioned modifications of the invention are important if the measurement device is in the form of an immersion probe for measurements on material in the form of paste or powder.

The real difficulty of the microwave measurement device lies in fulfilling the following two mutually contradictory requirements:

1. The depth of penetration of the microwaves into the sample must be sufficiently large to achieve a sufficiently high measurement sensitivity and to cover a representative sample volume;
2. On the other hand the radiation of the microwaves out into space must be avoided.

In practice it has proved that these two requirements can be reconciled. The new device has proved itself eminently suitable for precise moisture measurement in the above mentioned materials. A measurement accuracy of approximately 3% of the measurement range final value can be regarded as adequate. The sensitivity is so unexpectedly high that even the residual moisture range can be covered. Residual moisture is usually understood to mean moisture values in the range of from approximately 0.1 to 10% by weight. If the measurement head is designed as an immersion or insertion probe, the moistness of powder or paste form material can be determined by simple means. In addition the measurement of soil moisture is an important area of application for this type of measurement head. For this purpose the microwave resonator in the form of an insertion probe is lowered inside a guide tube in the soil.

Embodiments of the invention are described in more detail in the following with reference to the accompanying drawings, in which:

FIGS. 9 and 7B show the diagram of the design of a measurement resonator incorporated in a guide roller for strip form measurement material.

Figure 1:
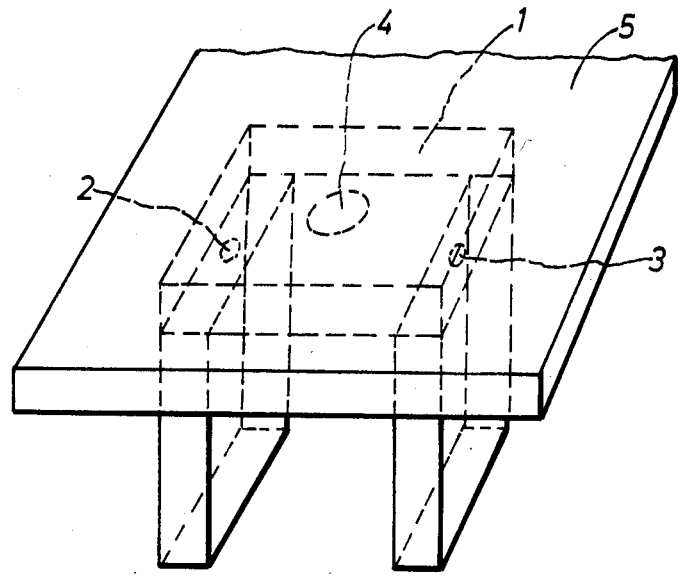
FIG. 1 shows the basic arrangement of resonator and sample.

Since the maximum of the microwave absorption for the free water molecule is approximately $10^{10}$ Hz, the frequency of the microwave generator is set in this range to achieve the largest possible measurement effect. Then commercial microwave components can be used for the X-band. The measurement principle can be seen from FIG. 1. The resonator 1 is a one-part rectangular resonator in which the $TE_{10n}$ field type is excited. It is connected to the microwave generator via an iris coupler 2. The output is connected via a similar iris coupler 3 to the microwave detector. In the centre of the top surface of the resonator there is located a circular perforation or opening 4 having a diameter of 10 mm at a point of predominantly electrical field strength (E field maximum). However the perforation can advantageously be aligned so that the magnetic field component passed primarily outwards. The requirement that the perforation should be $<\lambda/2$ is fulfilled at a microwave length of 3 cm. The sample to be examined, in this case a large panel 5, is guided over the resonator 1 or alternatively the resonator 1 may be applied to a wall. With these dimensions, the scattered field enters the sample to a depth of approximately $\lambda/10$. In this way radiation damping is prevented. In the unloaded state the resonator 1 achieves a quality of approximately 900. This permits the sensitive measurement of the residual moisture of paper, wood, brick work, concrete etc. A precondition for accurate moisture measurement is the smallest possible air gap between the application surface of the resonator and the surface of the measurement object. In the case of substantial surface roughness and large thickness of the measurement objects it may be useful to design the apparatus for a lower frequency, e.g. 2 GHz.

Figure 2:
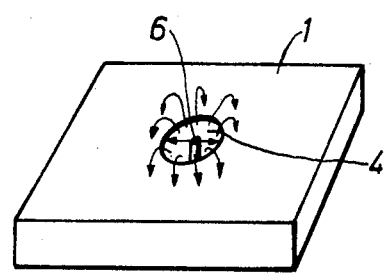
FIG. 2 shows the field distribution in the vicinity of the perforation outside the resonator.
Figure 2A:
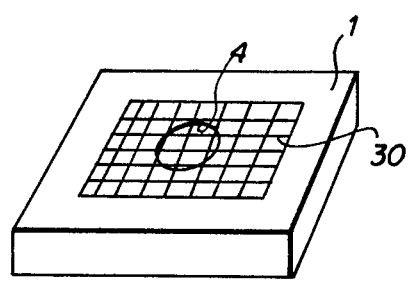
FIG. 2A shows a modified embodiment wherein the perforation is covered by a wire lattice.

FIG. 2 shows the electrical field distribution in the vicinity of the perforation 4, if additionally a conductor 6 in the form of a wire is arranged in the centre of the perforation in the longitudinal direction of the tube. The length of the piece of wire is generally equal to the diameter of the perforation 4. The resultant electrical scattered field results from a superimposition of the issuing E-field, of the $TE_{10}$ field type and also as a result of the fields of the wall currents flowing in the wire-form conductor. The wire form conductor effects a better concentration of the scattered field onto the sample area. The perforation does not necessarily need to be circular. Different shapes of perforations e.g. rectangular shapes are electrically equivalent but have the disadvantage of being mechanically more difficult to produce. Instead of one perforation of larger diameter, several of smaller diameters can also be provided, if the measurement is intended to extend over a larger area of the sample. Use can be made of the possibilities of an additional field concentration if it is determined that the quality variation of the cavity resonator is not only conditioned by dielectric losses of the sample, but there is also a contribution due to radiation damping. FIG. 2A shows a modified embodiment wherein a wire lattice 30 is positioned over the perforation or opening 4.

Figure 3:
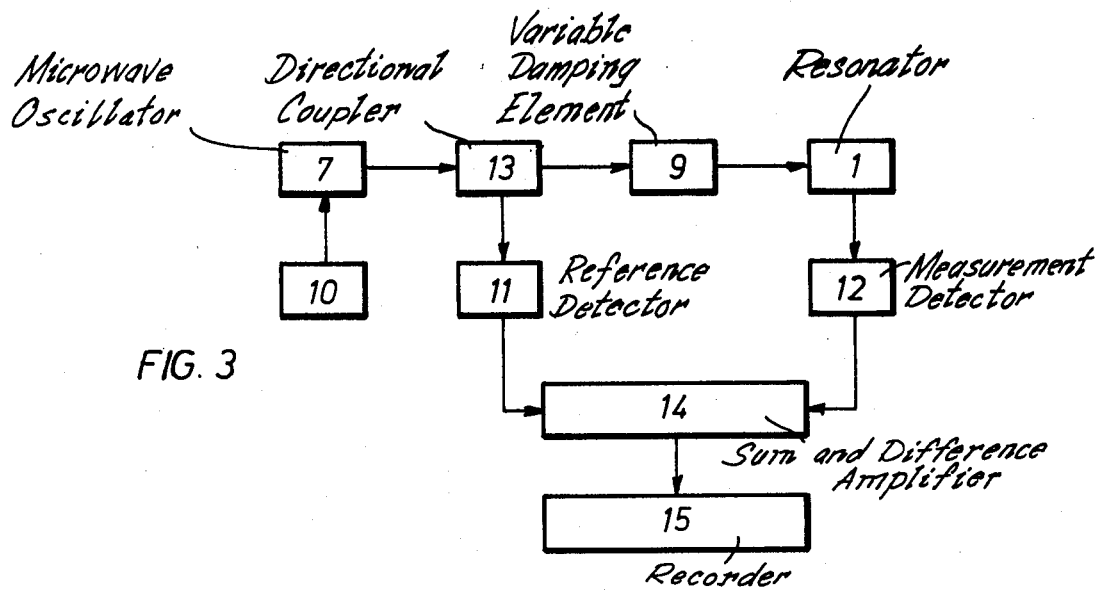
FIG. 3 shows the basic circuit diagram of the measurement arrangement in transmission.

FIG. 3 shows a block circuit diagram for the transmission arrangement indicated in FIG. 1. As already described, the resonator 1 is coupled via the iris coupler 2 to the microwave generator 7 and on the output side to the receiver 12. The degree of coupling depends on the diameter of the iris bores and influences the quality factor of the resonator. In this way the measurement sensitivity can be adjusted via the geometry of the iris couplers 2 and 3. In order to avoid interference from reflective signals, the microwave circuit leading to the resonator 1 is connected via a one way circuit.

Figure 4:
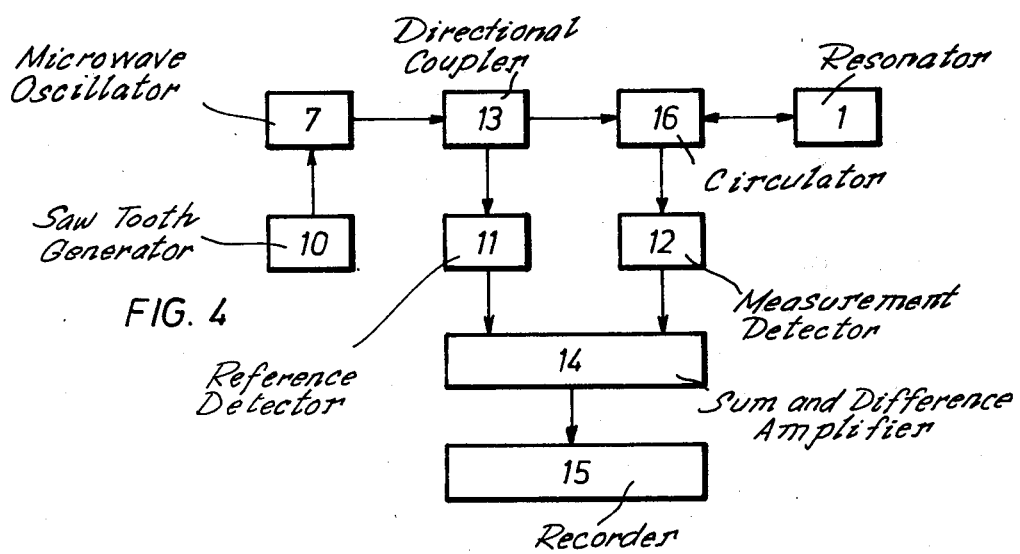
FIG. 4 shows the basic circuit diagram of the measurement arrangement in reflection.

In the following the microwave measurement arrangement is described with reference to the basic circuit diagrams (FIGS. 3 and 4). FIG. 3 shows a transmission circuit. The transmission resonator 1 is supplied via a variable damping element 9 from the microwave oscillator 7. As the microwave oscillator 7 a Varactor-modulated Gunn diode oscillator is used, which is frequency modulated by a saw tooth generator 10 in time linear manner. The generator or oscillator 7 may comprise a Hewlett Packard Model No. 8690 microwave generator and the sawtooth generator 10 may comprise a Hewlett Packard Model No. 8692b sawtooth generator. The variable damping element 9 may comprise a Narda Model No. 791FM element. The microwave output delivered is approximately constant in the frequency range covered. The modulation frequency is approximately 2KHz. The choice of a relatively high modulation frequency has the advantage that even rapid measurement value variations can be picked up. This is important for example in the case of large moisture variations along a panel shape sample. In practice, a modulation frequency between 50 Hz and 5 KHz is adequate. The frequency fluctuation of 150 MHz at 9 GHz carrier frequency is measured in such a way that the resonance curve of the resonator when empty and when supplied with the measurement object can safely be covered (see FIG. 5). The microwave output of the oscillator 7 is supplied via a directional coupler 13 to the reference detector 11 and via the variable damping element 9 to the microwave resonator 1 switched into transmission. The directional coupler 13 may comprise a Hewlett Packard Model No. 779D coupler and the reference detector 11 may comprise a Hewlett Packard Model No. 423A detector. The transmission signal (resonance curve of the resonator) is rectified and received from the measurement detector. 12. The receiver 12 may comprise a Hewlett Packard Model No. 423A receiver.

Figure 5:
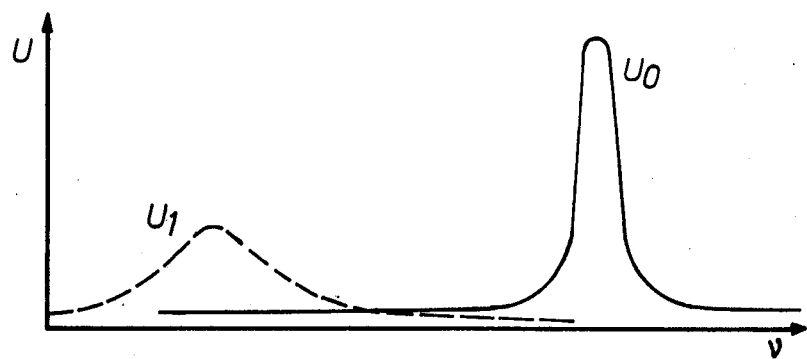
FIG. 5 shows the resonance curves of the resonator when empty and when damped and detuned by the applied sample.

It has the form shown in FIG. 5. With an increasing water content, the peak amplitude $U_1$ decreases and at the same time a displacement of the resonance frequency towards lower frequencies is associated with it. Let the peak amplitude of the detector signal for the resonator with and without sample be $U_1$ and $U_0$ respectively. The reference detector supplies the signal $U_R$. The signal $U_1$ and thus $U_1-U_R$ is a monotonic decreasing function of the quality factor and thus of the material moisture content. That is, as noted below, $U_1$ is inversely proportional to Q, the quality factor and therefore the quantity $U_1-U_R$ will decrease with increasing Q. With the directional coupler 13 a reference signal is derived and rectified by the reference detector 11. The reference detector 11 and the measurement detector 12 are peak voltage rectifiers. The rectifier peak voltage values $U_1$ and $U_R$ are then supplied to the sum and difference amplifier 14. Indication is effected with a measurement instrument 15 or a recording device. The sum and difference amplifier 14 may take the form as that shown in Analog Device Application Notes AN 4-4 and AN 31-1 and the recorder 15 may comprise a Hewlett Packard Model No. 3435A recorder. The bridge circuit (comparison branch consisting of directional coupler 13 and reference detector 11) has the advantage that fluctuations of the ambient temperature or of the output of the microwave oscillator 7 have practically no effect on the measurement accuracy.

Instead of a transmission arrangement, naturally a reflection circuit can also be used (FIG. 4). In this case a circulator 16 is arranged before the reflection resonator 1 which passes on the signal reflected by the resonator to the measurement detector 12. The circulator 16 may comprise a Valvo T 50/3000-N circulator. For small damping variations caused by dielectric loss of the water contained in the sample, the water content $c_{H2O}$ can be determined using the formula:

$$c_{H2O} = k\epsilon'' = f[\delta(\tfrac{1}{Q})] \quad \text{with } \delta(\tfrac{1}{Q}) = 1/Q_1 - 1/Q_o$$

(ASTM-Standards 13 (1964) 465, W. Eckhardt et al, Zs. angew. Physik 6 (1954) 236).
where
  $\epsilon''$ represents the imaginary portion of the dielectric constant DK of water
  $Q_1$ represents the quality of the resonator with a sample
  $Q_0$ represents the quality of the resonator without a sample.

The water content is therefore a clear function of the resonator quality. For absolute measurements this function must be calibrated. For this purpose, samples having a known water content are applied to the top surface of the resonator.

Figure 6:
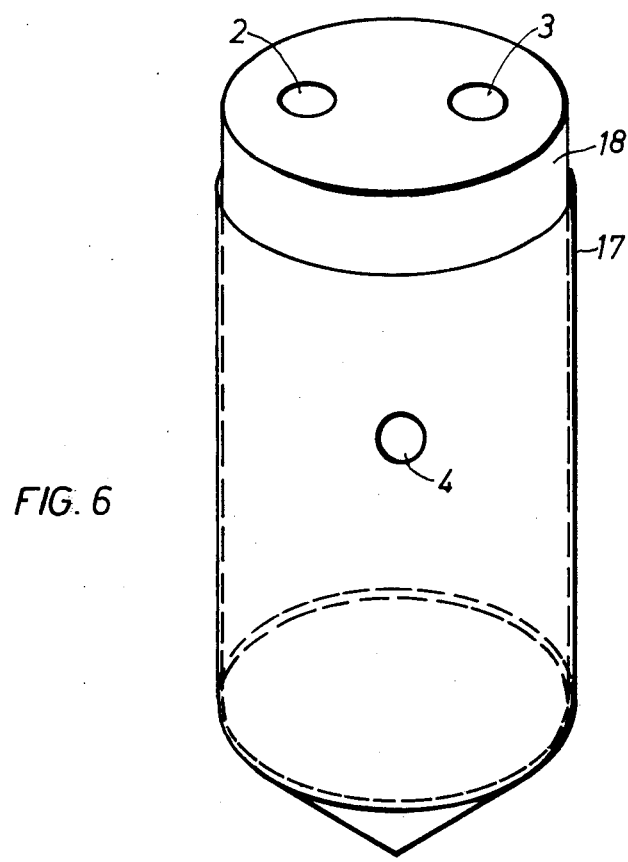
FIG. 6 shows an embodiment in which the resonator is in the form of an insertion probe.

The resonator according to FIG. 6, designed as an insertion probe serves for the moisture determination of powder or paste form material. It can in addition be used for the determination of the soil moistness in a specific stratum. For this purpose the insertion probe is lowered into the soil for example in a polytetrafluoroethylene tube 17. The measurement head is in the case formed by a cylindrical resonator 18, in which the $TE_{113}$ wave is excited. The perforated couplers 2 and 3 for the coupling and decoupling of the microwave energy are here arranged next to one another. The perforation 4 is located in the generatrix of the resonator 18. In the measurement of powder form materials, the resonator is sealed with PTFE disc (polytetrafluoroethylene), so that no sample material enters the resonator. For the same reason the resonator can also be completely filled with PTFE. The dielectric losses of this material are in the frequency range of 10 GHz and thus negligible.

Figure 7A:
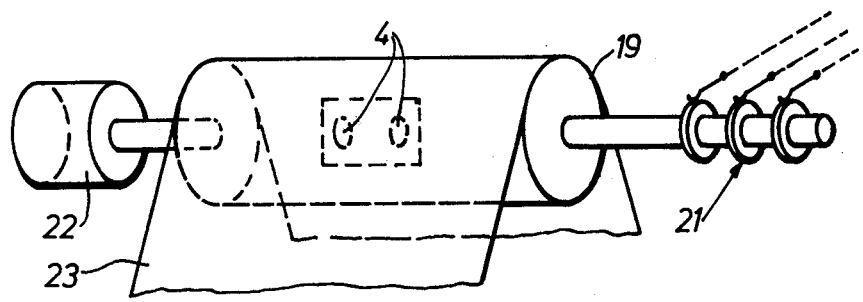
Figure 7B:
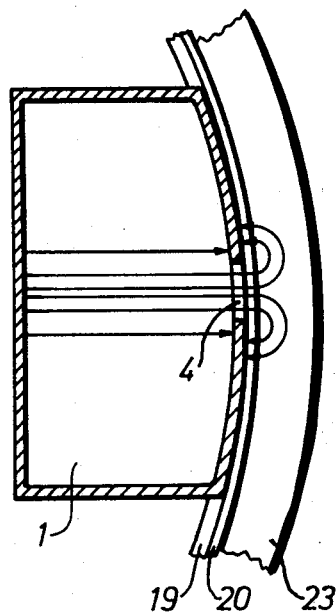

The incorporation of a scattered field probe into a roller 19 used to guide the product for the moisture measurement of flat continuously moving material (see FIG. 7a) e.g. paper or fabric webs, offers certain advantages relative to the use of two-part resonators (see for example German Offenlegungsschrift No. 2,340,130). Since measurement takes place from one side only there is no measurement gap limiting the product form. As a result the measurement frequency can be freely chosen without taking into consideration the measurement gap distance. In the case of the two part resonator the measurement gap distance and the frequency cannot be freely chosen, since it is not possible to go below a measurement gap distance to avoid radiation λ/2. To measure high and medium water contents, to achieve a calibration curve as linear as possible and for economic reasons one will work at for example from 2 to 9 GHz, while for sensitive residual moisture measurement and to eliminate competing absorptions (e.g. other dipole molecules, semi-conductors) frequencies of up to approximately 22 GHz are used. The use of the scattered field probe because of the limited depths of penetration of the measurement radiation also offers the advantage that assuming a sufficient thickness of the product, thickness variations do not affect the measurement result. By incorporating the scattered field probe in a guide roller according to FIG. 7 the possibility is obtained of alternately recording the measurement value (when the product lies on the scattered field outlet) and of the zero value when the scattered field opening is released by the product after the continued rotation of the roller 19 (see FIG. 7). The angle of looping of the measurement roller 19 should be approximately 90°. The alternately recorded measurement values $U_1$ and $U_0$ can be used for the precise characterisation of the moisture value $U_0-U_1$ as described above and for the standardisation of the measurement arrangements, so that a reference detector can be dispensed with. The incorporation of the scattered field probe in the measurement roller (see FIG. 7b) is effected in such a way that the perforation 4 in the resonator wall emitting the scattered field is in alignment with the surface of the roller. A covering 20 of a dielectrically low-loss material of low water absorption, e.g. PTFE, on the roller surface is also possible.

Figure 7C:
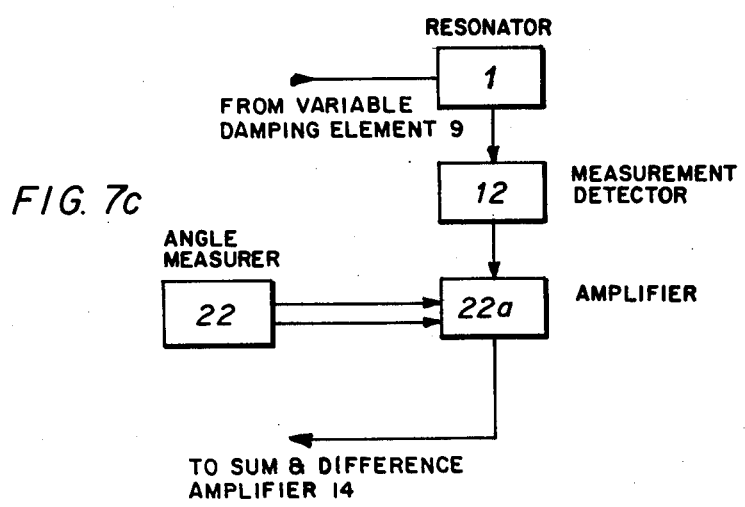
FIG. 7C is a partial schematic wiring diagram for use with the guide roller shown in FIG. 7A.

The whole microwave arrangement can usefully be located inside the roller so that only direct current signals have to be transferred via sliding contacts. However it is also possible to supply the microwave signal via revolving couplings. The advantage of this arrangement from the point of view of measurement technique is that the measurement and zero signal can be recorded alternately. To separate the measurement and zero signals, an amplifier connected as an electrical separator is used, which is controlled by the angle measurer in the following manner. During the time $t_1$ the signal $U_1$ is picked up and during the time $t_0$ the signal $U_0$ is picked up. $t_1$ is the time during which the perforations 4 are covered by the web 23 and $t_0$ is the time during which they are free. $t_1$ and $t_0$ are associated with corresponding switching positions of the angle measurer 22. The angle measurer 22 may comprise the angle encoder of Fa. TWK-electronik Kessler & Co. The circulator may be obtained from Valvo GmbH, D-2000, Hamburg 1, Burchardstrasse, Germany W. The angle encorder may be obtained from Kessler & Co., Heinrichstrasse 85, 4000 Dusseldorf, Germany. Thus, as shown in FIG. 7C, the angle measurer 22 is connected to an amplifier 22a, connected as a signal separator, between the detector 12 and the sum and difference amplifier 14. Accordingly, depending on the orientation of the opening 4 with respect to the web as detected by angle measurer 22, the signal conducted to the amplifier 14 will be either $U_1$ or $U_0$.

What we claim is:

1. Apparatus for the measurement of the moisture content of a sample comprising:
   generator means for generating a frequency modulated microwave signal,
   a one-part cavity resonator connected to said generating means,
   said resonator having an opening adapted to be closed by the sample to be measured and having a diameter no larger than a half wavelength in the frequency range of operation,
   said opening being positioned at the point of maximum field intensity of one out of the electrical and magnetic fields, whereby scattered field energy passes therethrough into the sample,
   said generating means being operable to generate a first signal at the resonance frequency of said resonator with said opening in the open state, and a second signal at the resonance frequency of said resonator with said opening closed by the sample,
   and receiving means receiving said first and second signals for measuring the water content of the sample,
   said receiving means comprising a peak amplitude detector for detecting the peak amplitude of said first and second signals, and comparing means for comparing said peak amplitude signals to obtain the water content of the sample.

2. A device as claimed in claim 1, wherein the resonator is a rectangular resonator having a $TE_{10n}$ field type.

3. A device as claimed in claim 1, wherein the resonator is a cylindrical resonator having a $TE_{11n}$ field type.

4. A device as claimed in claim 1, wherein a conductor in the form of a wire is arranged in the centre of the opening parallel to the longitudinal direction of the resonator, whose length is equal to the diameter of the perforation.

5. A device as claimed in claim 1, wherein the perforation is covered with a wire lattice.

6. A device as claimed in claim 1, wherein the perforation is covered with a polytetrafluoroethylene material.

7. A device as claimed in claim 1, wherein the resonator is filled with polytetrafluoroethylene as a dielectric.

8. A device as claimed in claim 1, wherein the resonator forms part of a guide roller for a flat sample and the opening for the outflow of the scattered field is integrated into the roller surface and the whole microwave electronic system is housed inside the roller.

9. A device as claimed in claim 8, wherein for the separate representation of the rotational angle dependent first and second signals separation amplifier means controlled by a rotational angle measurer is connected between said resonator and said receiver.

10. A method for the determination of the water content in a sample by the application of microwave energy thereto, comprising:
    positioning an opening having a diameter no larger than a half wavelength in the frequency range of operation in said resonator at a point of maximum field strength of one out of said electric and magnetic fields,
    locating the sample adjacent said opening so that the field passing through said opening is received by the sample,
    applying a frequency modulated microwave signal at constant intensity to said resonator,
    sweeping the frequency of said microwave signal through a band including the frequencies of resonance of said resonator with and without said sample adjacent said opening,
    detecting the signals from said resonator,
    rectifying said signals to obtain the peak amplitude thereof,
    and comparing the peak amplitude of said detected microwave signal at resonance with the sample adjacent said opening with the peak amplitude of said detected microwave signal at resonance with said opening uncovered to measure the water content in said sample.

11. The method as in claim 10, including the step of calibrating said resonator by positioning at least a sample having a known water content adjacent said opening, and relating the compared peak amplitudes obtained thereby with said known water content.

12. The method as in claim 10, including the step of covering said opening with polytetrafluoroethylene prior to positioning the sample adjacent said opening.

13. The method of claim 10, in which said opening is circular; said method further including the step of providing a wire conductor having a length substantially equal to said diameter, and positioning said wire conductor in the center of said opening with the length of said wire extending in the longitudinal direction of said resonator.

14. The method of claim 10, including the step of rotating said resonator with respect to the sample to periodically move said opening into and out of proximity to said sample, and synchronizing the detection of said peak amplitudes with respect thereto.

* * * * *